(12) United States Patent
Melsheimer et al.

(10) Patent No.: US 7,963,987 B2
(45) Date of Patent: Jun. 21, 2011

(54) SEQUENTIAL IMPLANT DELIVERY SYSTEM

(75) Inventors: Jeffry S. Melsheimer, Springville, IN (US); Mark A. Magnuson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 716 days.

(21) Appl. No.: 11/966,369

(22) Filed: Dec. 28, 2007

(65) Prior Publication Data

US 2009/0171427 A1 Jul. 2, 2009

(51) Int. Cl.
*A61F 2/06* (2006.01)
(52) U.S. Cl. .................................... 623/1.11
(58) Field of Classification Search ............... 623/1.11, 623/1.12, 1.2, 1.16; 606/108
See application file for complete search history.

(56) References Cited

U.S. PATENT DOCUMENTS

| | | | | |
|---|---|---|---|---|
| 5,702,418 A * | 12/1997 | Ravenscroft | | 623/1.11 |
| 5,833,694 A * | 11/1998 | Poncet | | 623/1.11 |
| 5,935,135 A * | 8/1999 | Bramfitt et al. | | 623/1.11 |
| 6,123,723 A * | 9/2000 | Konya et al. | | 623/1.11 |
| 7,137,993 B2 * | 11/2006 | Acosta et al. | | 623/1.11 |
| 7,241,308 B2 * | 7/2007 | Andreas et al. | | 623/1.11 |
| 7,294,146 B2 * | 11/2007 | Chew et al. | | 623/1.12 |
| 2002/0156496 A1 * | 10/2002 | Chermoni | | 606/194 |
| 2004/0093061 A1 * | 5/2004 | Acosta et al. | | 623/1.11 |
| 2004/0220585 A1 * | 11/2004 | Nikolchev | | 606/108 |
| 2004/0249435 A1 * | 12/2004 | Andreas et al. | | 623/1.12 |
| 2007/0043419 A1 * | 2/2007 | Nikolchev et al. | | 623/1.11 |
| 2007/0156223 A1 * | 7/2007 | Vaughan | | 623/1.11 |
| 2007/0265637 A1 * | 11/2007 | Andreas et al. | | 606/108 |

* cited by examiner

*Primary Examiner* — Gary Jackson
*Assistant Examiner* — Erin Colello
(74) *Attorney, Agent, or Firm* — Brinks Hofer Gilson & Lione (57) ABSTRACT

A method and device includes advancing a first stent and a second stent into a stenosed region of a blood vessel to protect or shield the vessel from possible blockage. The delivery device may include placement rings, selectively engagable by positioning members disposed on the outer wall of in inner catheter. The positioning members and the placement rings may be utilized to accurately place multiple stents within an afflicted vessel, in a single invasive procedure.

16 Claims, 7 Drawing Sheets

SEQUENTIAL IMPLANT DELIVERY SYSTEM

BACKGROUND

The present invention relates generally to devices, methods and systems for vascular treatment. One embodiment of the device includes a sequential implant delivery system using a plurality of placement rings to place sequential self-expanding stents and embolic protection devices within a vessel wall.

Vascular diseases and disorders are widespread health problems affecting many people. There are many chronic and acute diseases and disorders relating to the vascular system including, for example, thrombosis, embolism, aneurysm, atherosclerosis, arterioscholerosis, infarction and still others.

Heart attacks and strokes are leading health concerns. Obstruction of blood flow and/or vessel rupture may cause inadequate blood supply to the heart, brain, and other parts or all of the body. Occlusive diseases involving constriction, narrowing or obstruction of a blood vessel often present serious, possibly life-threatening risks. Additionally, complications in vascular treatment(s) may themselves necessitate further treatment. Some such risks include formation of emboli, vessel damage, thrombogenesis, blood loss, hemorrhage, and others. Furthermore, trauma and other injuries may damage the vascular system and often require repair or replacement.

At present, treatment of vascular disease, damage and disorders suffers from limitations, drawbacks and risks. The invention provides unique treatments and solutions to treatment of the foregoing and other problems.

BRIEF SUMMARY

The endovascular device described below may overcome the aforementioned problems and relates to a medical device, and more particularly, to a sequential implant delivery device that allows the practitioner to utilize more than one self-expanding stent at a time.

One embodiment includes a method for using a sequential delivery device, comprising introducing a device into an organ, the device including an inner catheter, a first stent, at least a second stent, a placement ring, and an outer sheath. The first stent includes a proximal end, a distal end, an exterior surface, and an inner lumen. The second stent includes a proximal end, a distal end, an exterior surface, and an inner lumen. The placement ring may be disposed between the proximal end of the first stent and the distal end of the second stent and the inner catheter includes a plurality of positioning members disposed axially along a longitudinal axis of the inner catheter. The method further includes disposing the device within a specified region of the organ, the distal end of the second stent being positioned approximately adjacent the proximal end of the first stent and unsheathing the first stent within said organ. The method further includes advancing the second stent through the organ and unsheathing the second stent.

The method described above wherein the specified region of the organ is a blood vessel afflicted with a stenosis.

The method described above wherein the first stent is a self expanding stent, and wherein the first stent expands when the outer sheath is withdrawn toward the proximal end of the blood vessel to expose the first stent.

The method described above wherein the second stent is a self expanding stent, and wherein the second stent is at least partially expanded upon withdrawal of the outer sheath.

The method described above wherein the second stent is a self expanding stent, the second stent being at least partially expanded upon withdraw of the outer sheath, and wherein the method further includes post-dilating the second stent with an inflation device.

The method described above wherein the inflation device is a balloon catheter.

The method described above wherein the positioning members are integrally formed along the longitudinal axis of the inner catheter.

The method described above wherein the positioning members comprise a plurality of flanges, protruding from an exterior surface of the inner catheter in a distal direction, at an angle less than 90 degrees.

The method described above wherein the positioning members comprise a plurality of barbs, protruding from an exterior surface of the inner catheter in a distal direction, at an angle less than 90 degrees.

The method described above wherein the positioning members comprise a locking member protruding in a vertical plane, and wherein the placement ring comprises a receiving cavity in the vertical plane, wherein the receiving cavities correspond with the locking members.

The method described above wherein the step of positioning said device within the vessel further comprises positioning the locking members out of alignment with respect to the receiving cavities and advancing the inner catheter and the placement rings along the longitudinal axis.

Another embodiment includes a sequential implant delivery device, including an inner catheter, a first stent, a second stent, at least one placement rings, and an outer sheath. The inner catheter includes a plurality of positioning members disposed axially along a longitudinal axis of the inner catheter. The first stent includes a proximal end, a distal end, an exterior surface, and an interior lumen and the second stent includes a proximal end, a distal end, an exterior surface, and an interior lumen. The placement ring is disposed between the distal end of the second stent and the proximal end of the first stent and the placement rings, the first stent, and the second stent are selectively movable along a longitudinal axis of the inner catheter.

The device described above wherein the positioning members selectively engage the placement rings.

The device described above wherein the positioning members engage the placement rings when the inner catheter is advanced in a distal direction.

The device described above wherein the positioning members are defined by a plurality of flanges, spaced along the longitudinal axis of the inner catheter.

The device described above wherein the flanges protrude from an exterior surface of the inner catheter in a distal direction, at an angle less than 90 degrees.

The device described above wherein the positioning members comprise a plurality of barbs, protruding from an exterior surface of the inner catheter in a distal direction, at an angle less than 90 degrees.

The device described above wherein the positioning members comprise a locking member protruding in a vertical plane, and wherein the placement ring comprises a receiving cavity in the vertical plane, wherein the receiving cavities correspond with the locking members.

The device described above wherein the locking members are rotatable to be unaligned with the receiving cavities, thereby enabling the inner catheter and the placement rings to be advanced along the longitudinal axis.

DETAILED DESCRIPTION

An example of a sequential delivery device and method for protecting and reinforcing blood vessels afflicted with stenosis is shown in FIGS. 1-7d. The device and method may include the use of at least two structural stents, delivered to a vessel in the same delivery system or similar device. In order to properly place the aforementioned stents, it may be necessary to utilize a method of maneuvering the respective stents independently of one another.

Figure 1:
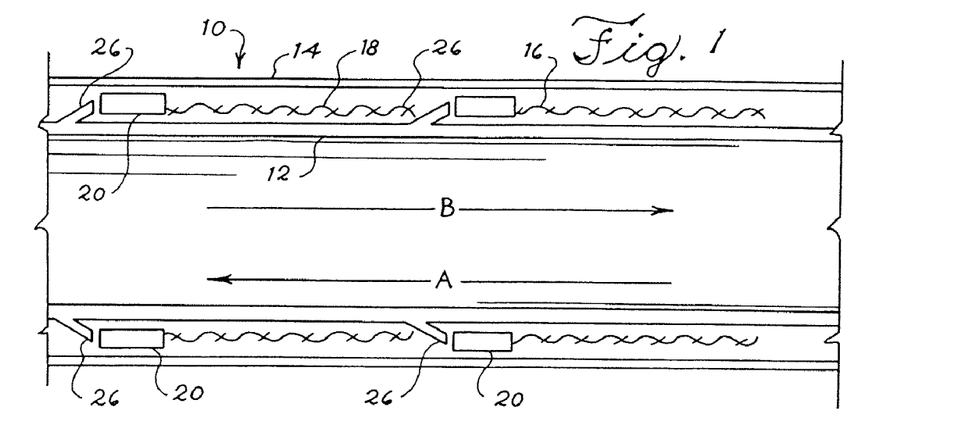
FIG. 1 is a side view of one example of a delivery device of the present invention.

One example of a sequential delivery device is described below, but it should be understood that any sequential delivery device may be used with the inner catheter and placement rings described herein. Referring now to FIG. 1, one example of a sequential implant delivery device 10 may include a ratcheting-type inner catheter 12, an outer sheath 14, a first stent 16, a secondary stent 18, and at least one free floating placement device or ring 20.

In one embodiment, the first stent 16 and the secondary stent 18 are loaded into the delivery device 10 over the inner catheter 12 in a compressed condition. Generally, the stents may be loaded into the delivery device 10 from the device's proximal end 22. However, the stents could be loaded into the delivery device 10 from either end using known techniques.

As shown in FIG. 1, after the first stent 16 is loaded into the delivery device 10 and positioned toward the distal end 24 of the device 10, the secondary stent 18 may also be loaded into the device 10, behind the first stent 12. The second stent 18, like the first stent 16, may generally be a self expandable vascular stent. However, the second stent 18 could also be a balloon expandable vascular stent, or any other suitable device.

Generally, the outer sheath 14 of the delivery device 10 covers the secondary stent 18, the first stent 16, and the inner catheter 12, preventing premature expansion of the stents.

Figure 2:
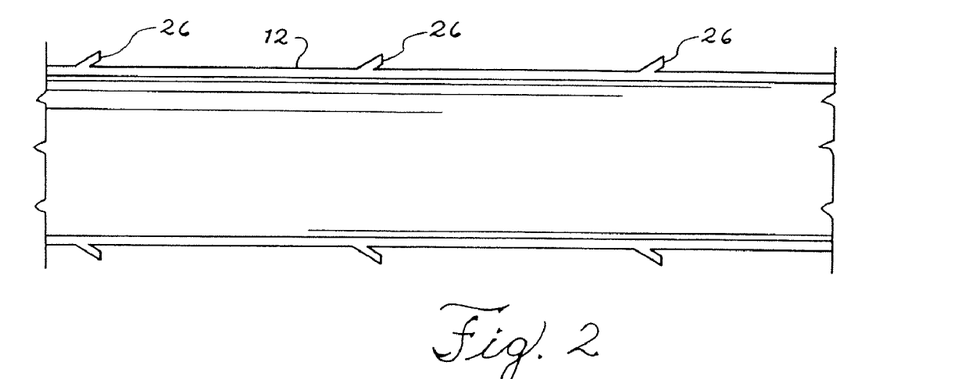
FIG. 2 is an inner catheter of the present invention.

Referring now to FIGS. 1 and 2, the inner catheter 12 may include features, such as a plurality of spaced apart flanges 26 that extend upwardly, in the distal direction and allow the catheter to function in a ratcheting manner. The flanges 26 may be pre-formed in the inner catheter body 12, or may otherwise be cut from or attached to an existing inner catheter tube 12. In practice the flanges 26 will form an angle α with the wall of the inner catheter 12 which is preferably less than 90 degrees.

Placement members or rings 20 may be disposed between or just distally of the respective flanges 26. In one embodiment, at least one of the rings 20 is free floating in the delivery device. The term "floating" will be used herein to describe a placement ring that is not permanently affixed to any part of the delivery system.

In one embodiment, and referring to FIG. 1, when the inner catheter 12 is pulled in the direction of arrow A, the flanges 26 may flatten against the outer wall of the inner catheter 12, allowing the placement rings 20 and the stents 16, 18 to slide along the longitudinal axis of the inner catheter 12 without engaging the flanges 26. If, however the inner catheter 12 is pushed in the direction of arrow B, the flanges 26 may engage the placement rings 20, advancing both the rings 20 and the corresponding stent 16, 18 through the delivery device 10 and out of the outer sheath 14, allowing a self-expanding stent 16, 18 to deploy in the blood vessel. Alternatively, the outer sheath 14 may be withdrawn along the direction of arrow A with respect to the inner catheter 12, which will have the same effect as pushing the inner catheter in the direction of arrow B. These methods are described more fully below in connection with FIGS. 7a-d, below.

Figure 3:
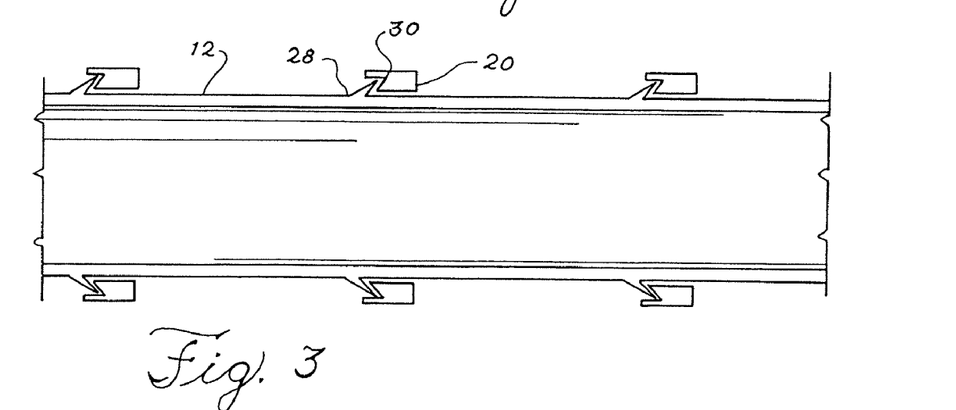
FIG. 3 is a side view of one example of an inner catheter and placement members of the present invention.
Figure 4:
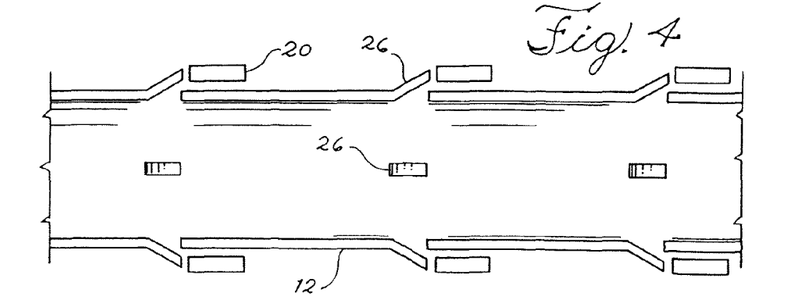
FIG. 4 is a side view of one example of an inner catheter and placement members of the present invention.

FIGS. 3 and 4 show alternative embodiments of an inner catheter 12. The embodiments shown in FIGS. 3 and 4 may be used similarly to that of FIG. 2. As shown in FIG. 3, the inner catheter 12 may include a plurality of barbs 28, formed or cut in the wall of the catheter 12. These barbs 28 may engage corresponding notches 30 formed in the proximal ends of the placement rings 20, selectively advancing the placement rings 20 through the delivery system 10 when the inner catheter 12 is advanced further into the vessel.

Similarly, in FIG. 4, the inner catheter 12 may include a plurality of flanges 26, as described in connection with the embodiment shown in FIGS. 1 and 2. It is contemplated that the flanges 26 may be spaced along the longitudinal axis of the inner catheter 12 in a variety of embodiments and placements, along either a vertical or horizontal plane, or both.

Figures 5, 6, 8:
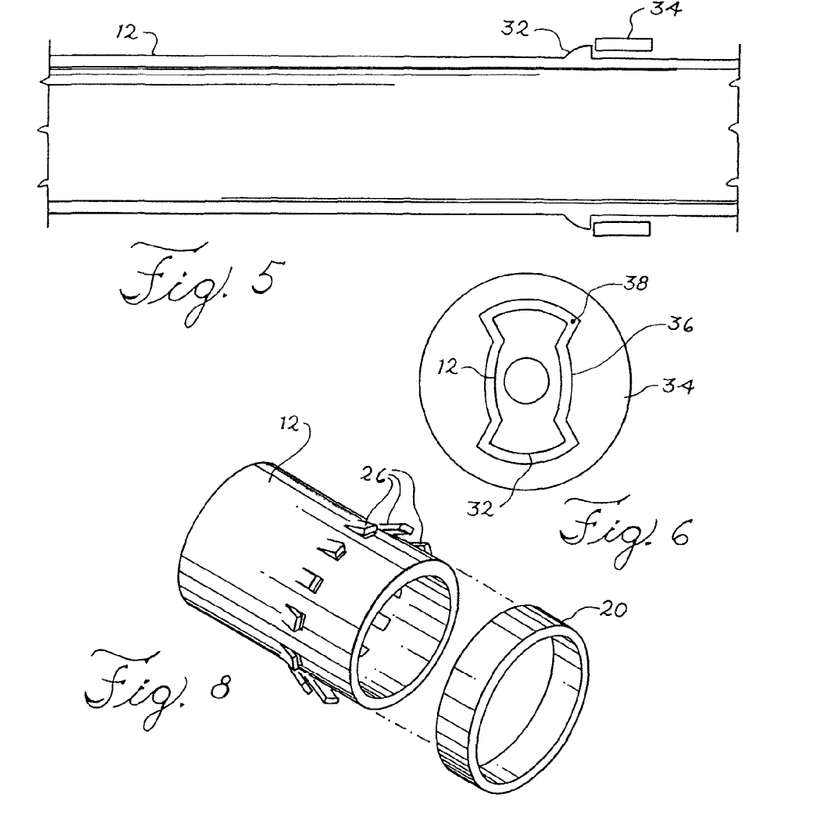
FIG. 5 is a side view of one example of an inner catheter and placement members of the present invention.
FIG. 6 is a cross section of the inner catheter and placement rings, as shown in FIG. 4.
FIG. 8 is a front perspective view of an inner catheter of the present invention.

Referring now to FIGS. 5 and 6, one embodiment of a delivery device may include an inner catheter 12 that employs a quarter-turn feature that selectively engages rotationally dependent placement ring(s) 34 based upon the catheter's 12 rotational alignment. As shown in FIG. 5, the catheter 12 may include at least one, and desirably two locking members 32, that protrude from the outer surface of the catheter 12. The locking members 32 may be positioned on opposite surfaces of the generally round catheter device 12.

Referring now to FIG. 6, the inner surface 36 of the rotationally dependent placement rings 34 may be formed to fit and move past the shape of the locking member 32 on the inner catheter 12 when the locking member 32 and the rotationally dependent placement ring 34 are similarly aligned.

The respective placement ring 34 may be designed to have corresponding receiving cavities 38 within its inner surface, on opposite surfaces of the ring 34. When both the locking member(s) 32 and the rings 34 are similarly aligned, as shown in FIG. 6, the ring 34 will slide past the locking member 32.

Figure 7A:
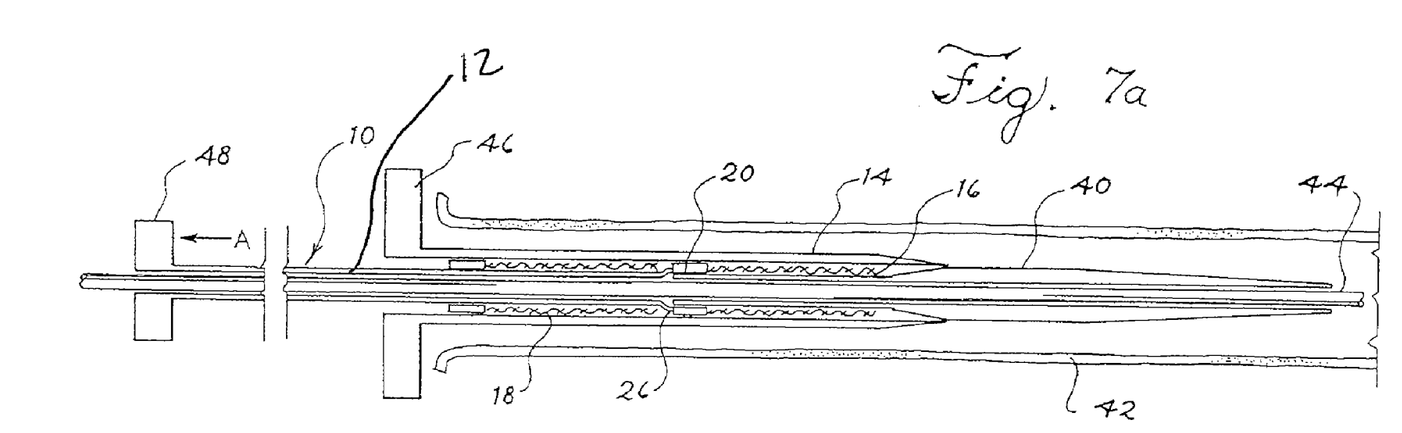
FIG. 7a is a side view of a stent assembly advanced through a stenosed region of a blood vessel in an initial position.

Referring now to FIGS. 7a-d, a delivery device may be used to effectively launch multiple stent devices within the blood vessel of a patient. Referring to FIG. 7a, the inner catheter 12 may also include a tip 40. The tip 40 retains the placement rings 20 on the inner catheter 12 after they have been used to deploy a stent. In other words, the tip 40 keeps the rings 20 from sliding off the distal end of the inner catheter 12 and becoming emboli within the blood vessel. Secondly, the tip 40 provides a smooth, step-free transition between the outer sheath 14 and the inner catheter 12 during introduction.

The tip 40 could be a flexible tip, a guiding tip, a cannula or another tip or tips of differing size, shape, and structure. The tip 40 may generally be made of a soft material, such as polyurethane, and may be attached only to the inner catheter 12.

With reference to FIG. 7a, there is shown an illustrative view of a delivery system 10 disposed within a blood vessel 42 and effectively placed at the initial position of deployment. A guidewire 44 may be positioned within the organ to be treated with its distal end advanced through and past the distal end of the region to be treated. Generally, the guidewire 44 may be as small as 0.014 inches in diameter.

Once the guidewire 44 is positioned within the vessel 42, the delivery device 10, including the inner catheter 12, the outer sheath 14, the first stent 16, the secondary stent 18 and the placement rings 20, is threaded over the guidewire 44. The tip 40 of the inner catheter 12, as well as the distal end of the outer sheath 14, may include a radiopaque marker used for positioning purposes. In this manner, the tip 40 of the inner catheter 12 can be positioned distally of the region to be treated. The first stent 16 and the secondary stent 18 may also include radiopaque markers at either end. The markers may be in the form of gold rivets on the terminating eyelets of the stent bodies.

The proximal end of the delivery device 10, including the outer sheath 14 and the inner catheter 12, may be attached to handles. The handles are generally located outside of the patient's body and allow the sheath 14 and the inner catheter 12 to be moved independently of, or relative to, one another. The handles may include a hub 46 attached to the proximal end of the outer sheath 14, allowing the user to withdraw the outer sheath 14 in the direction of arrow A. In addition, the inner catheter 12 may be attached to an inner shaft, control rod, push rod, or the like 48 and may be disposed through the hub 46. The user may be able to hold the inner catheter 12 in place, while the hub 46 pulls the outer sheath 12 in the direction of arrow A. Alternatively, the inner catheter 12 may be moved in the direction of arrow B by moving the inner catheter 12 in and out of the hub 46, holding the control rod 48 for support.

In FIG. 7a the loaded delivery device 10 has been moved into the deployment or initial position. Once the loaded delivery device 10 is in place, using the handles the user may begin to withdraw the outer sheath 14 relative to the first stent 16 and the secondary stent 18, in the direction of arrow A. Other deployment techniques and devices are also contemplated.

Figure 7B:
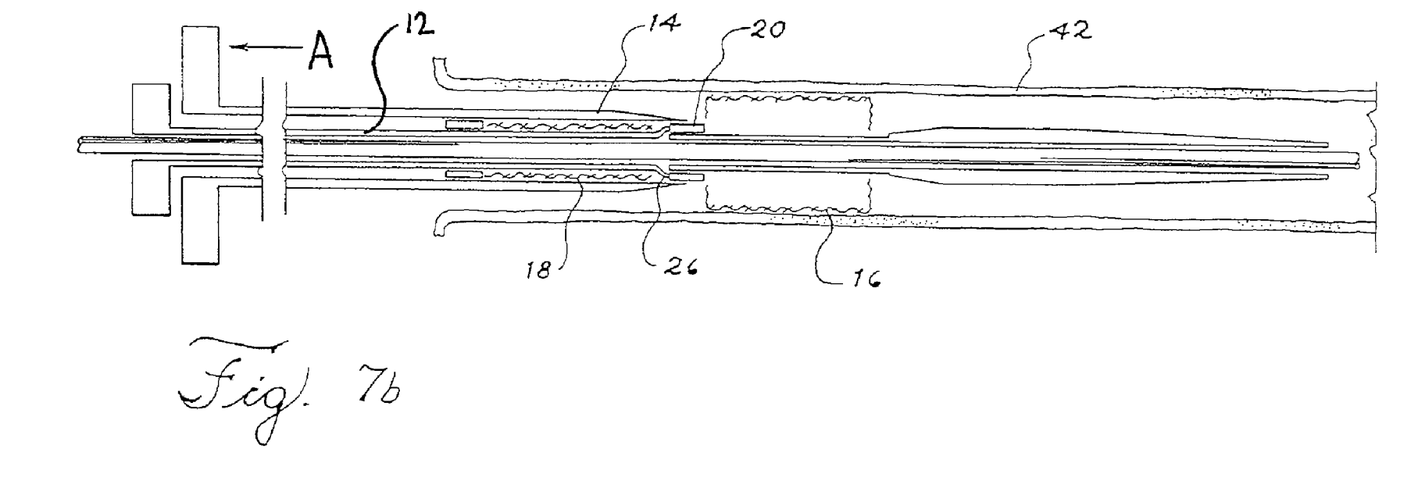
FIG. 7b is a side view of a stent assembly advanced through a stenosed region of a blood vessel in a second position.

As shown in FIG. 7b, once the outer sheath 14 has been withdrawn in the direction of arrow A to a secondary position, the first stent 16 will deploy into the vessel. The first stent 16 and the secondary stent 18 will be prevented from moving proximally, the same direction of the outer sheath 14, by the placement rings 20 disposed within the delivery system 10. The placement rings 20 desirably float freely within the delivery device 10 and are themselves impeded from proximal movement by the flanges 26 disposed on the inner catheter 12.

In this embodiment the placement members 20 are rings that extend around the body of the inner catheter. This configuration allows the members 20 to support each surface of the individual stents, in order to prevent deformation. The placement rings may be the translational interface between the intermittent barbs of the inner catheter, and the proximal face of a given stent. The end faces/surfaces of the stents are not uniform, and therefore require the continuous and un-interrupted face of the placement ring bearing against it to distribute the force evenly through as many points of contact as possible.

Alternatively, it is contemplated that the placement members may be replaced by a ring of, or multiple individual, flanges placed around or formed into the body of the inner catheter, as shown in FIG. 8. Multiple or continuous flanges may support the end faces of the stents much like a placement ring.

Figure 7C:
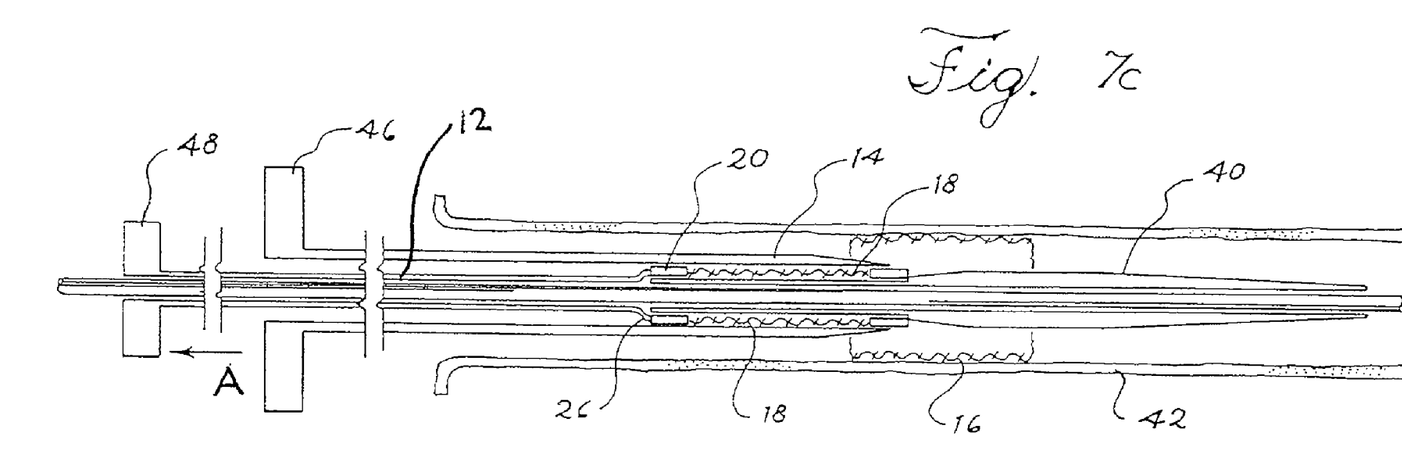
FIG. 7c is a side view of a stent assembly advanced through a stenosed region of a blood vessel in a third position.

As shown in FIG. 7c, the inner catheter 12 may then be withdrawn in the direction of arrow A~while the outer sheath 14 is stationary. The inner catheter 12 may be withdrawn so that the tip 40 is adjacent the distal placement ring 20. The placement rings 20 and the secondary stent 18 remain in place while the flanges 26 on the inner catheter 12 are compressed distally and both the inner catheter 12 and compressed flanges 26 are moved proximally through the center lumen of the rings 20 and the stent 18. The inner catheter 12 may be moved a measured distance in order to dispose the distal flange 26 behind the proximal placement ring 20a.

Once the tip 40 has been withdrawn into the third position, the secondary stent 18 may then be advanced distally over the inner catheter 12 by pushing flange 26, the positioning ring 20 and the stent through the vessel. The secondary stent may be disposed within the vessel so that when deployed, the distal end of the secondary stent 18 overlaps with the proximal end of the first stent 16. This is only one example of stent placement within the vessel, but many others are contemplated using the method described above.

Figure 7D:
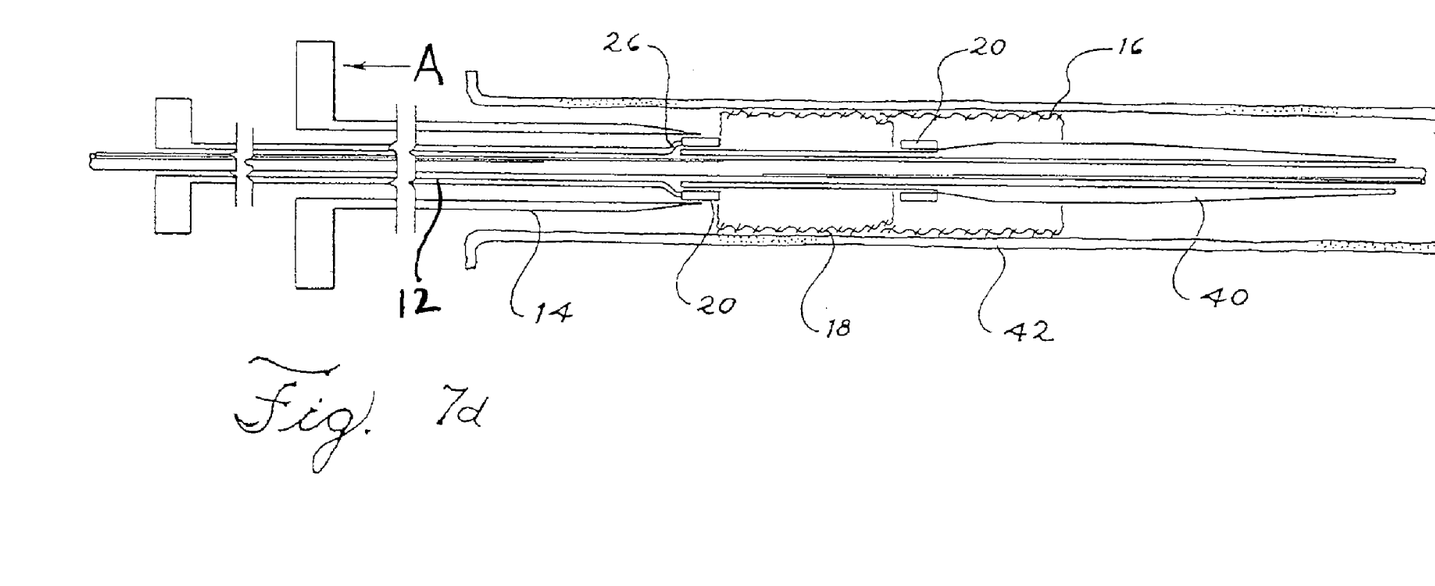
FIG. 7d is a side view of a stent assembly advanced through a stenosed region of a blood vessel in a fourth position.

Referring now to FIG. 7d, the there is illustrated deployment of the second stent 18. Once the secondary stent 18 has been advanced through the vessel 42, the outer sheath 14 may again be withdrawn in the direction of arrow A, thus exposing the secondary stent 18 to the inner surface of the vessel 42. Again, the self expanding secondary stent 18 expands as it exits the sheath 14. The delivery device, including the outer sheath 14 and inner catheter 12, may then be removed from the patient's body.

Figure 9:
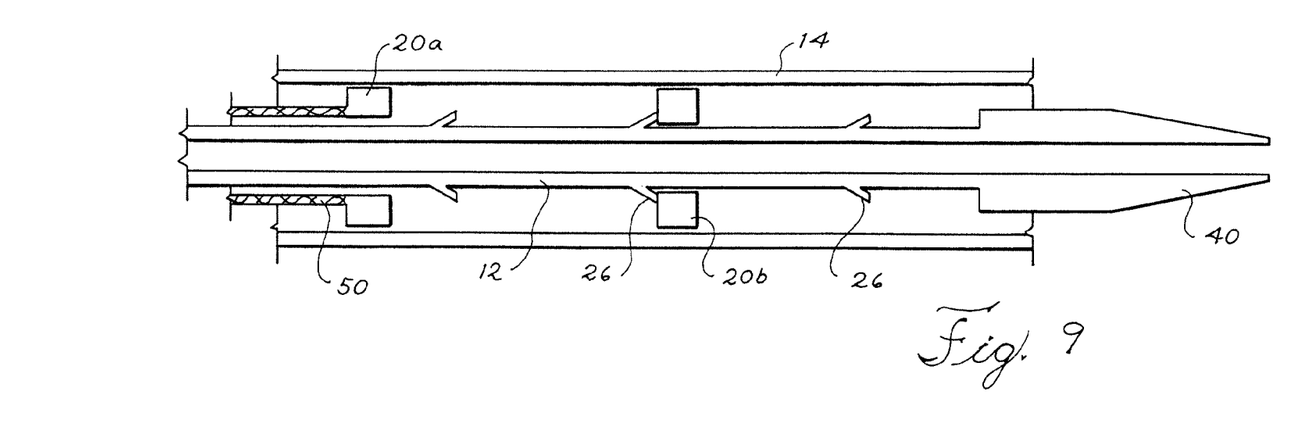
FIG. 9 is a front perspective view of a delivery device of the present invention.

Alternative embodiments of the delivery system include using a tertiary catheter 50, secured to the most proximal placement ring 20a. As shown in FIG. 9, the proximal ring 20a would be secured to a tertiary catheter 50 such that the inner catheter 12 moves independently of the proximal placement ring 20a. This allows the floating distal ring 20b to ratchet forward as the inner catheter 12 is moved proximally.

Figure 10:
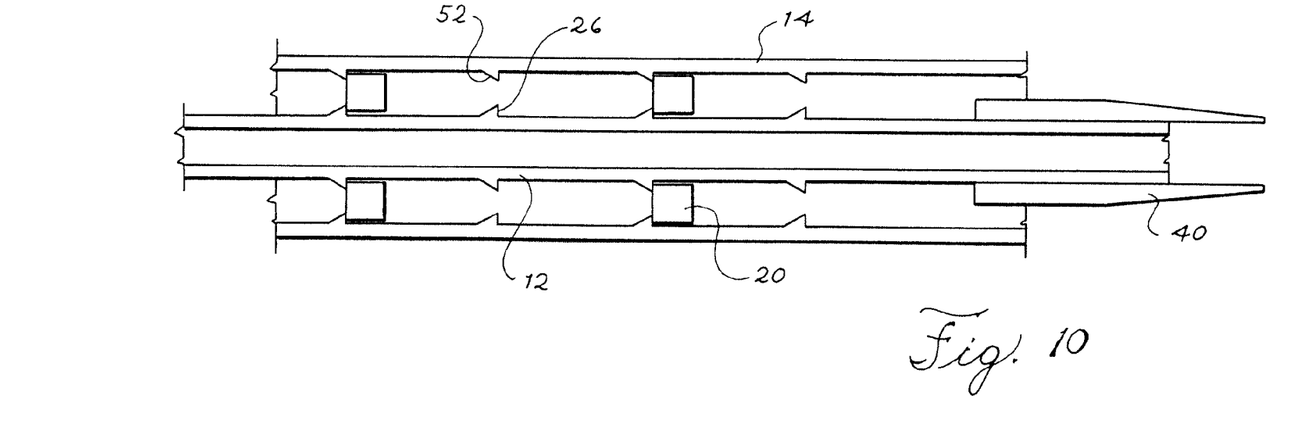
FIG. 10 is a front perspective view of a delivery device of the present invention.

Another embodiment may be the use of a delivery device that includes an inner catheter 12 and an outer sheath, both having flanges placed on the outer and inner surfaces, respectively. As shown in FIG. 10, the outer sheath 14 may also include flanges 52 similar to that of the inner catheter 12 but on the inside surface. This configuration prevents the floating rings 20 from moving in the proximal direction when the inner catheter 12 is pulled in the proximal direction.

Figure 11:
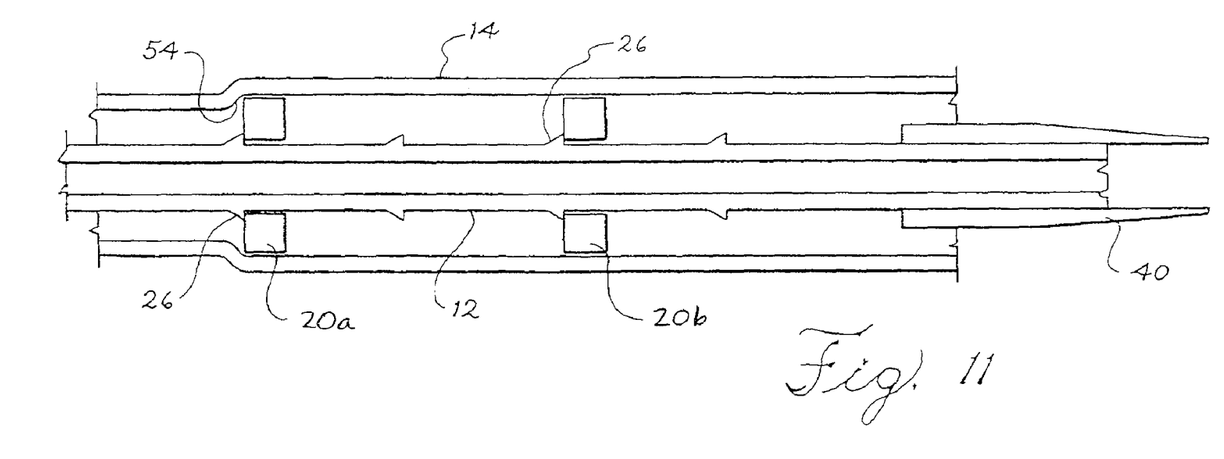
FIG. 11 is a front perspective view of a delivery device of the present invention.

Another embodiment of the delivery device includes a dual diameter outer sheath 14. Referring now to FIG. 11, the outer sheath 14 may be formed using a stepped mandril providing an impingement surface 54 for the proximal ring 20b. The proximal ring 20a will thereby remain stationary during proximal movement of the inner catheter 12.

Figure 12:
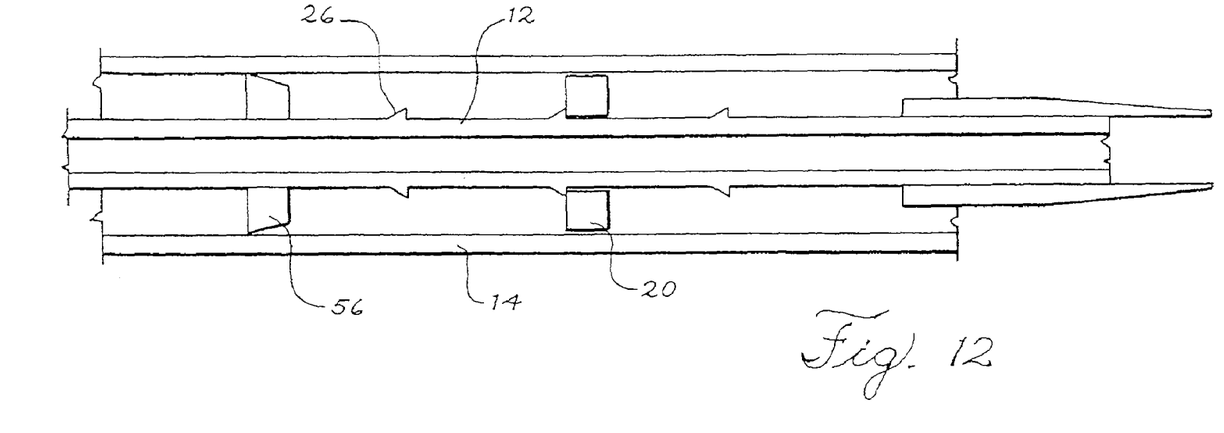
FIG. 12 is a front perspective view of a delivery device of the present invention.

Yet another embodiment of the delivery device includes a uni-direction placement ring 56, in addition to the floating ring 20. As shown in FIG. 12, the proximal ring 56 may be shaped in such a way that the ring 56 and the outer sheath 14 can only move in one direction with respect to each other another.

Figure 13:
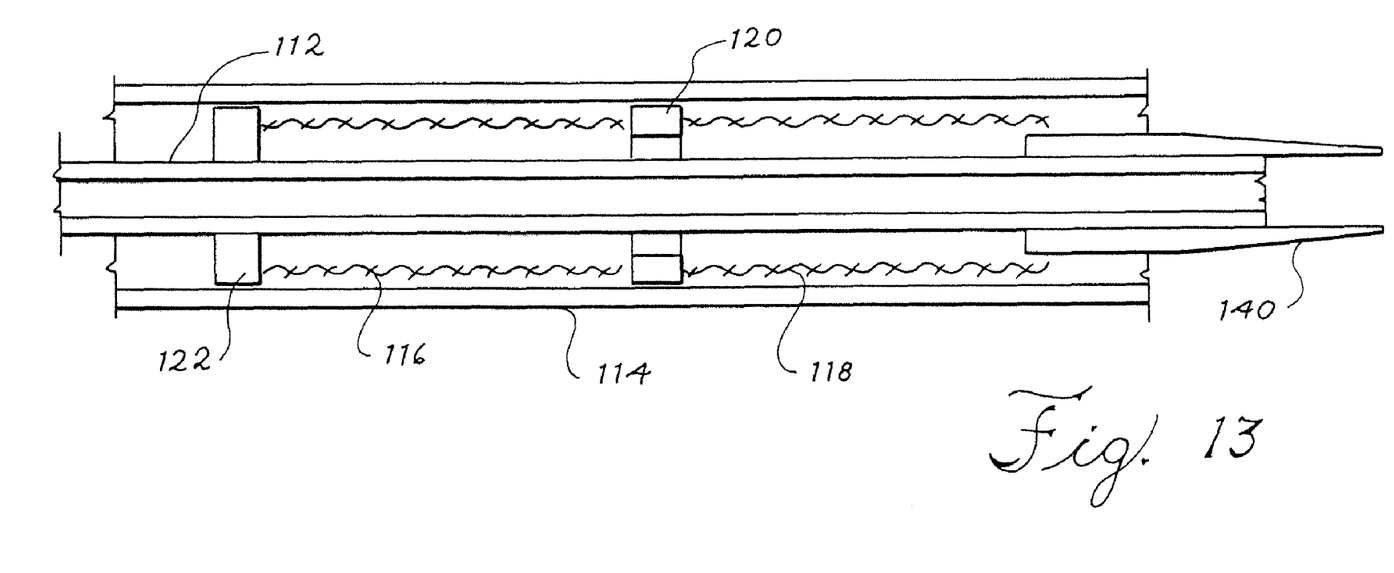
FIG. 13 is a front perspective view of a delivery device of the present invention.

Finally, it is contemplated that the floating placement rings 120 may be utilized in a delivery device 100 with or without the ratcheting-type inner catheter 12. Assembly of a delivery system 100 with such a floating ring 120 can be achieved by ensuring that the inner diameter of the ring 120 is less than the outer diameter of the attached tip 140. As shown in FIG. 13, multiple stents, 116 and 118, may be loaded in to the outer sheath 114 of the delivery device 100, over the inner catheter 112, with floating rings 120 between each of the stents. At the very proximal end of the device 100, at least one ring 122 may be affixed to the inner catheter 112.

It is intended that the foregoing detailed description be regarded as illustrative rather than limiting, and that it be understood that it is the following claims, including all equivalents, that are intended to define the spirit and scope of this invention.

We claim:

1. A method for using a sequential delivery device, comprising:
    introducing a device into an organ, said device including an inner catheter, a first stent, at least a second stent, a floating placement ring, and an outer sheath; said first stent having a proximal end, a distal end, an exterior surface, and an inner lumen;
    said second stent having a proximal end, a distal end, an exterior surface, and an inner lumen;
    said inner catheter having at least one member extending radially outward from an outer surface thereof to a first diameter, said member extending partially around a circumference of said inner catheter; and
    said placement ring being disposed between said proximal end of said first self-expanding stent and a distal end of said member, wherein said placement ring comprises a first portion and a second portion, said first and second portions defining a receiving cavity, wherein said first portion has a second diameter that is greater than said first diameter of said member, and said second portion has a third diameter that is less than said first diameter of said member and greater than a diameter of said inner catheter,
    disposing said device within a specified region of said organ, said distal end of said second stent being positioned approximately adjacent said proximal end of said first stent;
    rotating said inner catheter to a first rotational position relative to said placement ring where said member is not aligned with said receiving cavity;
    unsheathing said first stent within said organ by moving said sheath proximally with respect to said inner catheter and engaging said member in said first rotational position such that said distal end of said member engages said proximal end of said placement ring and a distal end of said placement ring engages said proximal end of said first stent, said member and said placement ring thereby providing a force against said proximal end of said first stent and preventing said first stent from moving proximally relative to said inner catheter during deployment;
    advancing said second stent through said organ;
    rotating said inner catheter to a second rotational position relative to said placement ring where said member is aligned with said at least one receiving cavity;
    moving said placement ring along said inner catheter in said second position past said member; and
    unsheathing said second stent.

2. The method of claim 1, wherein said first stent is a self expanding stent, and wherein said first stent expands when said outer sheath is withdrawn toward said proximal end of said blood vessel to expose said first stent.

3. The method of claim 1, wherein said second stent is a self expanding stent, and wherein said second stent is at least partially expanded upon withdrawal of said outer sheath.

4. The method of claim 1, wherein said second stent is a self expanding stent, said second stent being at least partially expanded upon withdraw of said outer sheath, and wherein said method further includes post-dilating said second stent with an inflation device.

5. The method of claim 1, wherein said member is integrally formed along said longitudinal axis of said inner catheter.

6. The method of claim 1, wherein said member comprises a flange protruding from an exterior surface of said inner catheter in a distal direction, at an angle less than 90 degrees.

7. The method of claim 5, wherein said member comprises one or more barbs, said barbs protruding from an exterior surface of said inner catheter in a distal direction, at an angle less than 90 degrees.

8. The method of claim 1, wherein said device further includes a fixed placement ring disposed at said proximal end of said second stent.

9. The method of claim 8, wherein said first stent is a self expanding stent, and wherein said first stent expands when said outer sheath is withdrawn toward said proximal end of said blood vessel to expose said first stent.

10. The method of claim 8, wherein said second stent is a self expanding stent, and wherein said second stent is at least partially expanded upon withdrawal of said outer sheath.

11. The method of claim 8, wherein said second stent is a self expanding stent, said second stent being at least partially expanded upon withdraw of said outer sheath, and wherein said method further includes post-dilating said second stent with an inflation device.

12. A sequential implant delivery device, comprising:
    an inner catheter, a first stent, a second stent, at least a first and a second floating placement ring, and an outer sheath;
    said inner catheter having at least one member extending radially outward from an outer surface thereof to a first diameter, said member extending partially around a circumference of said inner catheter;
    said first stent having a proximal end, a distal end, an exterior surface, and an interior lumen; and
    said second stent having a proximal end, a distal end, an exterior surface, and an interior lumen;
    wherein said first and second placement rings are free from attachment to said inner catheter and said outer sheath, said first placement ring being disposed between said proximal end of said first stent and a distal end of said member;
    wherein said first and second placement rings, said first stent, and said second stent are selectively movable along a longitudinal axis of said inner catheter,
    wherein at least said first placement ring comprises a first portion and a second portion, said first and second portions defining a receiving cavity, wherein said first portion has a second diameter that is greater than said first diameter of said member, and said second portion has a third diameter that is less than said first diameter of said member and greater than a diameter of said inner catheter,
    whereby when said first placement ring is in a first rotational position relative to said member, said member is not aligned with said receiving cavity, wherein as said inner catheter is moved distally with respect to said outer sheath, said member engages said proximal end of said first placement ring and a distal end of said first placement ring engages said proximal end of said first stent, said member and said first placement ring thereby providing a force against said proximal end of said first stent and preventing said first stent from moving proximally relative to said inner catheter during deployment, and whereby when said first placement ring is in a second rotational position relative to said member, said member is aligned with said receiving cavity to allow said first placement ring to move proximally along said inner catheter past said member.

13. The device of claim 12, wherein said member comprises at least one flange.

14. The device of claim 13, wherein said device further includes a tertiary catheter affixed to a proximal placement ring.

15. The device of claim 12, wherein said outer sheath includes positioning members defined by a plurality of flanges, spaced along said longitudinal axis of an inner surface of said outer sheath.

16. The device of claim 12, wherein said outer sheath has a first inner diameter and a second inner diameter, creating an impingement surface for a proximal placement ring.

* * * * *